US005676928A

United States Patent [19]
Klaveness et al.

[11] Patent Number: 5,676,928
[45] Date of Patent: Oct. 14, 1997

[54] LIPOSOMES

[75] Inventors: Jo Klaveness, Oslo; Arne Berg, Sandvika; Trond Vegard Jacobsen, Oslo; Pal Rongved, Nesoddtangen; Thorfinn Ege, Tranby, all of Norway; Hiroshi Kikuchi; Kiyoto Yachi, both of Tokyo, Japan

[73] Assignees: Nycomed Imaging AS, Oslo, Norway; Daiichi Pharmaceutical Co., Ltd., Tokyo, Japan

[21] Appl. No.: 468,743

[22] Filed: Jun. 6, 1995

Related U.S. Application Data

[63] Continuation of PCT/GB95/00689, Mar. 27, 1995.

[30] Foreign Application Priority Data

Mar. 28, 1994 [JP] Japan ................................. 6-057480

[51] Int. Cl.$^6$ .................................................. A61K 9/127
[52] U.S. Cl. ........................... 424/9.321; 424/450; 424/94
[58] Field of Search ................... 424/450, 1.21, 424/9.51, 9.321, 9.4

[56] References Cited

U.S. PATENT DOCUMENTS

| | | | |
|---|---|---|---|
| 4,192,859 | 3/1980 | Mackaness et al. | 424/5 |
| 4,522,803 | 6/1985 | Lenk et al. | 424/1.1 |
| 4,863,717 | 9/1989 | Keana | 424/9 |
| 4,900,540 | 2/1990 | Ryan | 424/9 |

FOREIGN PATENT DOCUMENTS

| | | |
|---|---|---|
| 75933/91 | 11/1990 | Australia . |
| 0 494 616 A1 | 7/1992 | European Pat. Off. . |
| 2 437 831 | 4/1980 | France . |
| 88/09165 | 12/1988 | WIPO . |
| 89/11272 | 11/1989 | WIPO . |
| WO 90/04943 | 5/1990 | WIPO . |
| 91/10422 | 7/1991 | WIPO . |
| 91/09629 | 7/1991 | WIPO . |
| 92/10166 | 6/1992 | WIPO . |
| 9217212 | 10/1992 | WIPO . |
| 92/22247 | 12/1992 | WIPO . |

OTHER PUBLICATIONS

Chem. Pharm. Bull. 39(4) pp. 1018–1022(1991), vol. 39 No. 4, Possibility of Heat Sterilization of Liposomes, H. Kikuchi, A. Carlsson, K. Yachi and S. Hirota.

*Primary Examiner*—Gollamudi S. Kishore
*Attorney, Agent, or Firm*—Bacon & Thomas

[57] ABSTRACT

The invention provides a diagnostic composition for administration to human or animal subjects, the composition containing multilamellar liposomes, optionally together with unilamellar liposomes, the liposomes containing at least one imaging agent and being suspended in an aqueous medium containing said imaging agent, wherein the liposomes comprise a neutral phospholipid and a charged phospholipid, the average particle diameter of the liposomes is 50–3000 nm and the concentration of imaging agent in any aqueous phase filling the interior of the liposomes is substantially the same as that in the aqueous medium in which the liposomes are suspended. The contrast agents concerned are typically X-ray, MRI or ultrasound contrast agents.

19 Claims, No Drawings

LIPOSOMES

This application is a continuation of pending International Patent Application No. PCT/GB95/00689 filed Mar. 27, 1995.

This invention relates to diagnostic compositions for injection containing liposomes encapsulating one or more imaging agents.

Contrast agents are employed to effect image enhancement in a variety of fields of diagnostic imaging, the most important of these being X-ray imaging, magnetic resonance imaging (MRI), ultrasound imaging and nuclear medicine imaging.

In X-ray imaging, including applications such as computed tomography (CT) and digital subtraction angiography (DSA), contrast is based on differences in electron density. X-ray contrast agents in current use are generally based on heavy elements, and include barium salts such as barium sulphate, which may be used to enhance visualisation of the gastrointestinal system and iodinated contrast agents, which my be used in visualisation of the gastrointestinal system and in parenteral studies.

Iodinated X-ray contrast agents most commonly contain iodinated phenyl groups, typically possessing at least one 2,4,6-triiodophenyl group having at the 3- and/or 5-positions groups selected from carboxyl, carbamoyl, N-alkylcarbamoyl, N-hydroxyalkylcarbamoyl, acylamino, N-alkylacylamino and acylaminomethyl. Ionic X-ray contrast agents of this type include metrizoic acid, diatriazoic acid, iothalamic acid, ioxaglic acid and salts of these acids.

Non-ionic iodinated X-ray contrast agents, which in general are substantially less toxic than the ionic agents by virtue of their lower osmolality and consequent reduced haemodynamic effects, include iohexol, iopentol, iopamidol, iodixanol, iopromide, iotrolan and metrizamide. Included amongst these are the so-called dimers such as for example iodixanol and iotrolan which, by virtue of their osmolality, may be formulated to be isotonic with blood at concentrations of 300 mg I/ml or above.

Interest has recently been shown in parenteral X-ray contrast agents based on heavy metal clusters/chelates—see, for example, WO-A-9114460 and WO-A-9217215.

In view of their hydrophilic nature, all the heretofore-mentioned X-ray contrast agents have approximately the same extracellular biodistribution and therefore exhibit similar clinical indications and are renally excreted. Attempts have therefore been made to find more organ-specific contrast agents. Thus, for example, iodinatedphenyl groups have been linked to macromolecular substrates such as starch in the hope of improving the vascular half-life of iodinated contrast agents.

Potential liver contrast agents based on biodegradable particles have been proposed (see, for example, WO-A-8900988 and WO-A-9007491) and liposomes containing either ionic or non-ionic X-ray contrast agents have been suggested. No such agents have yet been marketed or have reached the stage of late clinical development because of stability or toxicity problems, and there is thus an unfulfilled need for more stable, non-toxic and organ-specific X-ray contrast agents.

The principal contrast parameters in MRI which can be manipulated by contrast agents are the spin relaxation time ($T_1$) and the spin spin relaxation time ($T_2$). Paramagnetic chelates, for example based on manganese (2+), gadolinium (3+) and iron (3+), reduce the spin lattice relaxation time ($T_1$) and thereby increase the signal intensity. MR contrast agents based on magnetic/superparamagnetic particles reduce the spin spin relaxation time ($T_2$), resulting in a decrease in signal intensity.

Paramagnetic chelates based on dysprosium and high doses of other paramagnetic compounds will also reduce the MR signal intensity. For a review of MR contrast agents, some of which are under development or on the market, see for example D. D. Stark and W. G. Bradley: Magnetic Resonance Imaging, Mosby 1992, Chapter 14.

Hydrophilic chelates such as GdDTPA, GdDOTA, GdHPDO3A and GdDTPA-BMA are distributed extracellularly and eliminated renally. Such compounds are useful in, for example, visualising lesions in the central nervous system. Other more organ- or tissue-specific agents include MnDPDP, GdBOPA, GdEOB-DTPA, paramagnetic porphyrins, macromolecular compounds, particles and liposomes.

Various paramagnetic metal ions and chelates have accordingly been incorporated into liposomes. Thus, for example, small unilamellar vesicles (SUVs), large unilamellar vesicles (LUVs) and multilamellar vesicles (MLVs) with varying lipid composition, surface charge and size have been proposed as MR contrast agents (see for example, S. E. Seltzer in Radiology 171 (1989) p. 19; S. E. Seltzer et al. in Invest. Radiol. 23 (1988) p. 131; C. Tilcock et al. in Radiology 171 (1989) p. 77; C. Tilcock et al. in Biochim. Biophys. Acta 1022 (1990) p. 181; E. C. Unger et al. in Invest Radiol. 25 (1990) p. 638; E. C. Unger et al. in Invest Radiol. 23 (1988) p. 928; E. C. Unger et al. in Radiology 171 (1989) p. 81; E. C. Unger et al. in Magn. Reson. Imaging 7 (1989) p. 417 and J. Vion-Dury et al. in J. Pharmacol. Exp. Ther 250 (1989) p. 111)). However, despite the profusion of reports on liposomal MR contrast agents, no such product is today commercially available or in late clinical development.

Ultrasonic imaging is based on penetration of ultrasound waves, e.g. in the frequency range 1–10 MHz, into a human or animal subject via a transducer, the ultrasound waves interacting with interfaces of body tissues and fluids. Contrast in an ultrasound image derives from differential reflection/absorption of the sound waves at such interfaces; results may be enhanced by the use of Doppler techniques, including the use of colour Doppler to evaluate blood flow.

It has long been realised that it may be advantageous to increase the difference in acoustic properties of different tissues/fluids using contrast agents, and since the use of indocyanine green in 1968 as the first ultrasound contrast agent many other potential contrast inducing agents have been examined. These include emulsions, solid particles, water-soluble compounds, free gas bubbles and various types of encapsulated gas-containing systems. It is generally accepted that low density contrast agents which are easily compressible are particularly efficient in terms of the acoustic backscatter they generate; gas-containing and gas-generating systems thus tend to exhibit markedly greater efficacy than other types of contrast agent.

Three ultrasound contrast agents are now commercially available or in late clinical development, these being Echovist®, based on gas-containing galactose microcrystals; Levovist®, comprising gas-containing galactose microcrystals coated with fatty acid; and Infoson®, which comprises gas bubbles encapsulated by partially denatured human serum albumin. Clinical use of these agents is restricted, however, by their short contrast half-lives (i.e. by their relative lack of stability in vivo) and/or their limited shelf life.

Accordingly, there is a continuing need for ultrasound contrast agents, especially for cardiac and non-cardiac perfusion studies, which combine good storage stability with stability in vivo, preferably for at least several passages of circulation in the case of cardiac and non-cardiac perfusion analysis.

In spite of the numerous publications which suggest the use of liposome formulations and other techniques to enhance tissue- or organ-specificity of various types of contrast agent, these all possess disadvantages and there are currently no products of this type on the market or in late clinical development. This would appear to be the result of problems involving low encapsulation efficacy, toxicity, insufficient shelf life and/or instability in vivo or short contrast half life; additionally, some of the existing products possess very complex compositions. There thus remains a need for contrast agents which overcome these problems. In the field of ultrasound imaging there is a particular need for contrast agents which exhibit sufficiently high in vivo stability for use in cardiac and non-cardiac perfusion and for agents stable enough to permit efficient liver imaging diagnosis.

In general, lipid-soluble drugs are easily incorporated in liposomes. On the other hand, among water soluble drugs, water soluble electrolytes can be encapsulated in the internal aqueous phase in liposomes by electrostatic interaction between the charge of the drug and the charged lipid (Japanese Patent Application No. 2-187370), or by a pH gradient between outside and inside of liposome (WPI 88-271022/38).

However, using the above methods the amount of encapsulated drug is low. Moreover, where the drug is a water soluble non-electrolytic substance, the above-mentioned means cannot be applied, and therefore it is not easy efficiently to encapsulate a water-soluble non-electrolyte in liposomes. As means for efficiently encapsulating a water-soluble non-electrolyte in the internal aqueous phase of liposomes, reverse-phase evaporation methods (Proc. Natl. Acad. Sci. U.S.A., Vol. 75(9), p 4194, 1978), ether injection methods (ibid, Vol. 443, p 629, 1975) and the like have been proposed.

However, since such methods use an ether having a low ignition point, these methods cannot be used for industrial production of large amounts of liposomes.

International Patent Application WO 88/09165 describes liposome preparations for injection containing an X-ray contrast agent solution within the liposomes and a buffered physiologically saline continuous phase in which the liposomes are suspended. Although the liposomes are formed in an aqueous medium containing the X-ray contrast agent, for injection they are isolated by centrifugation and resuspended in the buffer. It would be very beneficial if the liposome preparation could be autoclaved to provide sterile compositions for injection, since preparation of the formulation from the separate components of the mixture under aseptic conditions is expensive and unreliable; whilst in principle the liposome suspension may be sterile filtered this in practice is only applicable when the entire particle size distribution is below 0.22 μm. However, with few exceptions, autoclaving of liposome suspensions has not previously been successful due to the existence of a phase transition temperature (Tc) well below autoclaving temperatures (about 121° C.); such exceptions arise when the encapsulated solute and the lipid bilayers have opposite charges, as reported by Kikuchi et al. in Chem. Pharm. Bull. 39(4), pp 1018–1022 (1991). Thus, on autoclaving liposome preparations such as those of WO 88/09165, having X-ray contrast agent only in the inside of the liposomes, we have found that the X-ray contrast agent escapes from within the liposomes. We have further found that this problem can be avoided by autoclaving the liposomes in a continuous phase in which the concentration of dissolved X-ray contrast agent outside the liposomes is substantially equal to that in the liquid phase inside. Such autoclaving is normally effected in a sealed vessel which remains sealed after cooling and storage, until being opened immediately prior to injection.

The present invention is further based on the finding that liposomal contrast agents for use in imaging can be improved with regard to encapsulation efficacy, toxicity, production process and/or shelf life by using a neutral lipid and a charged lipid to form the liposome membrane and keeping the average particle diameter of the liposomes relatively small, e.g. in the size range 50 to 3000 nm. The liposomes carry a net negative charge which provides electrostatic repulsion between the liposome membranes leading to high encapsulation capacity, e.g. at least 5 ml/g.

According to one feature of the present invention we provide a diagnostic composition for administration to human or animal subjects, said composition containing multilamellar liposomes, optionally together with unilamellar liposomes, said liposomes containing at least one imaging agent and being suspended in an aqueous medium containing said imaging agent, wherein the liposomes comprise a neutral phospholipid and a charged phospholipid, the average particle diameter of the liposomes is 50–3000 nm and the concentration of imaging agent in any aqueous phase filling the interior of the liposomes is substantially the same as that in the aqueous medium in which the liposomes are suspended.

The compositions of the invention comprising liquid filled liposomes thus comprise an outer continuous phase of conventional contrast medium, which meets blood pool conventional imaging requirements as a general contrast agent, together with liposomes containing a contrast agent which will become localised in the liver and spleen and assist in imaging these organs.

Liposome suspensions according to the present invention have a high encapsulation capacity in the internal aqueous phase (e.g. at least 5 ml/g lipid, preferably at least 6 ml/g) and therefore are capable of holding a large amount of water-soluble drug, and are stable in the blood and on storage as well as against autoclaving.

Compositions of the invention for use in X-ray imaging may, for example, incorporate any of the iodinated X-ray contrast agents and heavy metal cluster/chelate X-ray contrast agents known in the art, e.g. as hereinbefore described.

Iodinated X-ray contrast agents in compositions according to the invention preferably contain three or more iodine atoms per molecule and commonly contain one or more iodinated phenyl groups. Non-ionic imaging agents are preferred, especially the so-called non-ionic dimers such as iodixanol and iotrolan, which are highly hydrophilic and generate only low osmotic pressure at high concentrations. The concentration of the contrast agent in the composition may vary widely and will be influenced by factors such as the nature of the contrast agent, the intended route of administration of the final composition and the clinical indication.

A typical concentration may, for example, be in the range 10–300 mg (preferably 60–180 mg, more preferably 70–110 mg) of encapsulated iodine per ml composition. The concentration of total iodine per ml of composition is preferably in the range 40–450 mg, more preferably 160 to 320 mg. The present compositions are usually intravenously administered and the administered dose of the composition may similarly vary widely, e.g. depending on the clinical indication;

generally, a typical dose for vascular or liver imaging may, for example, be in the range 5–300 mg iodine per kg bodyweight.

Heavy metal clusters/chelates in liposome preparations according to the invention preferably contain at least two metal atoms with atomic numbers higher than that of iodine; representative contrast agents of this type include, for example, the tungsten clusters/chelates described in WO-A-9114460 and WO-A-9217215. Non-ionic clusters/chelates may be preferred.

Compositions of the invention for use in MR imaging may, for example, incorporate any of the paramagnetic agents known in the art, e.g. as hereinbefore described. Such paramagnetic contrast agents may, for example, be encapsulated in or covalently attached to the multicompartment vesicles, or incorporated non-covalently into the lipid membrane.

The paramagnetic contrast agent may, for example, be a physiologically acceptable paramagnetic metal salt or chelate or may comprise free radicals, preferably of the nitroxide type. Manganese (2+) salts are preferred where the paramagnetic agent is the free metal ion. Chelates are preferably based on manganese (2+), gadolinium (3+), dysprosium (3+) or iron (3+) and may contain chelating agents such as described in the literature (see e.g. WO-A-9110645), for example NTA, EDTA, HEDTA, DTPA, DTPA-BMA, BOPTA, TTHA, NOTA, DOTA, DO3A, HP-DO3A, EOB-DTPA, TETA, HAM, DPDP, porphyrins and derivatives thereof.

The concentration of such a paramagnetic agent in the composition may, for example, be in the range 1 mM–0.5M. The present MR contrast diagnostic compositions are usually intravenously administrated, and a typical dose for MR liver imaging would, for example, be 0.02 mmol of encapsulated metal chelate per kg bodyweight. Again both concentrations and dosages will be influenced by factors such as the nature of the paramagnetic agent, the intended route of administration and the clinical indication.

Liposome preparations for use in MR imaging may also incorporate, e.g. by encapsulation, superparamagnetic or ferromagnetic agents, e.g. such as are known in the art. Preferred agents of this type include magnetite, $\gamma$-$Fe_2O_3$, mixed ferrites and other iron-based compounds with magnetic properties, including organic ferromagnetic compounds. The encapsulated agent may be free or coated with, for example, dextran, a fatty acid or other biotolerable compound known to stabilize magnetic materials; where the product is for parenteral use the coating should also be biodegradable. The agent is conveniently in the form of an aqueous suspension of particles having particle size in the range 4 nm–1 μm, preferably 4–40 nm.

The concentration of such diagnostic agents may, for example, be in the range 0.01 mM–0.1M. Dosages will be influenced by the nature of the agent, its biodistribution and the clinical indication; a typical dose for vascular imaging (including perfusion) or liver imaging may, for example, be in the range 0.1–100 μmol encapsulated iron per kg bodyweight, in the case of intravenous administration.

Liposome compositions for use in ultrasound imaging may be used in all types of ultrasound techniques, including Doppler technology. Such compositions preferably comprise liposomes having a physiologically acceptable gas encapsulated therein or a gas precursor encapsulated therein or covalently attached thereto.

In general any biocompatible gas may be present in ultrasound compositions according to the invention, for example air, nitrogen, oxygen, hydrogen, nitrous oxide, carbon dioxide, or, more preferably, a water insoluble gas, for example helium, argon, sulphur hexafluoride, a low molecular weight optionally fluorinated hydrocarbon such as methane, acetylene, carbon tetrafluoride or a $C_{2-7}$ perfluoroalkane such as perfluoropropane, perfluorobutane or perfluoropentane, or a mixture of any of the preceding gases. The term "gas" as used herein includes any substance in gaseous form at the normal body temperature of 37° C. and therefore includes low temperature boiling liquids such as diethyl ether or certain perfluoroalkanes.

Gas precursors include aminomalonate; carbonates and bicarbonates such as lithium carbonate, lithium bicarbonate, sodium carbonate, sodium bicarbonate, ammonium carbonate, calcium carbonate and magnesium bicarbonate; physiolosically acceptable diazonium compounds; carbonate esters containing groupings of the type—$CO.O.CR^1R^2.O.CO.OR^3$; and β-ketoacids.

These may react in a variety of ways to generate gas-containing liposomes. Thus, for example, carbonates and bicarbonates may generate carbon dioxide in vivo following administration, in view of the acidic pH values prevalent in the body; diazonium compounds may be irradiated, e.g. with UV light, to generate nitrogen; carbonate esters will interact with non-specific esterases in vivo leading to elimination of carbon dioxide; β-ketoacids will decarboxylate spontaneously.

Ultrasound compositions according to the invention may, for example, be administered enterally or parenterally, although there may be advantages in particular applications in administration directly into body cavities such as the Fallopian tubes. In general, however, intravascular administration, most commonly by intravenous injection, is most likely to be employed, in order to enhance vascular imaging, including cardiac and extracardiac perfusion. Because of its stability, much of a composition so administered will ultimately undergo uptake by the reticuloendothelial system, mainly in the liver, thereby affording good liver ultrasound contrast enhancement.

Ease of compressibility is a desirable property of low density ultrasound contrast agents. Since the liposomes in the compositions of the invention essentially comprise non-solid matrices they will exhibit a substantial degree of flexibility. This accordingly will enhance the compressibility and thereby the echogenicity of gas-filled ultrasound compositions according to the invention.

One of the essential components for forming the membranes of the present liposomes is a neutral phospholipid comprising at least one substantially saturated fatty acid residue. The number of carbon atoms in such fatty acid residues is preferably at least 15 or more, preferably at least 16. Where the number of carbon atoms in a fatty acid residue is less than 14, the ability of the liposomes to hold the internal aqueous phase is low and the stability of the liposomes in blood after administration is low. On the other hand, where the number of carbon atoms in a fatty acid residue is 28 or more, biocompatibility becomes low, and very high temperature is necessary during production of liposomes.

Another of the essential components for forming the membranes of the present liposomes is a charged phospholipid comprising at least one substantially saturated fatty acid residue. The number of carbon atoms in such a fatty acid residue is usually at least 14, preferably at least 15 and more preferably at least 16. Where the number of carbon atoms in a fatty acid residue is less than 14, the ability of the liposomes to hold the internal aqueous phase is low and the stability of the liposomes in blood after administration is low. On the other hand, where the number of carbon atoms in a fatty acid residue is 28 or more, biocompatibility becomes low and very high temperature is necessary during production of liposomes.

The term "substantially saturated" as used above means that fatty acid residues of the neutral and charged phospholipids are fully saturated (i.e. contain no C—C double bonds) or that the extent of their unsaturation is very low, e.g. as shown by an iodine value of no more than 20, preferably no more than 10. Where the extent of unsaturation is too high, the liposomes are easily oxidized and are difficult to heat-sterilize.

Neutral phospholipids useful in the present invention include, for example, neutral glycerophospholipids, for example a partially or fully hydrogenated naturally occurring (e.g. soybean- or egg yolk-derived) or synthetic phosphatidylcholine, particularly semi-synthetic or synthetic dipalmitoyl phosphatidylcholine (DPPC) or distearoyl phosphatidylcholine (DSPC).

Charged phospholipids useful in the present invention include, for example, positively or negatively charged glycerophospholipids. Negatively charged phospholipids include, for example, phosphatidylserine, for example a partially or fully hydrogenated naturally occurring (e.g. soybean- or egg yolk-derived) or semi-synthetic phosphatidylserine, particularly semi-synthetic or synthetic dipalmitoyl phosphatidylserine (DPPS) or distearoyl phosphatidylserine (DSPS); phosphatidylglycerol, for example a partially or fully hydrogenated naturally occurring (e.g. soybean- or egg yolk-derived) or semi-synthetic phosphatidylglycerol, particularly semi-synthetic or synthetic dipalmitoyl phosphatidylglycerol (DPPG) or distearoyl phosphatidylglycerol (DSPG); phosphatidylinositol, for example a partially or fully hydrogenated naturally occurring (e.g. soybean- or egg yolk-derived) or semi-synthetic phosphatidylinositol, particularly semi-synthetic or synthetic dipalmitoyl phosphatidylinositol (DPPI) or distearoyl phosphatidylinositol (DSPI); phosphatidic acid, for example a partially or fully hydrogenated naturally occurring (e.g. soybean- or egg yolk-derived) or semi-synthetic phosphatidic acid, particularly semi-synthetic or synthetic dipalmitoyl phosphatidic acid (DPPA) or distearoyl phosphatidic acid (OSPA). Although such a charged phospholipid is commonly used alone, more than one charged phospholipid may be used. In the case where more than one charged phospholipid is used, preferably both the charged phospholipids are positively charged, or both the charged phospholipids are negatively charged, in order to prevent aggregation.

Positively charged lipids include, for example, an ester of phosphatidic acid with an aminoalcohol, such as an ester of dipalmitoyl phosphatidic acid or distearoyl phosphatidic acid with hydroxyethylenediamine.

According to the present invention, the ratio of the neutral phospholipid and the charged phospholipid is usually 200:1 to 3:1, preferably 60:1 to 4:1, and more preferably 40:1 to 5:1 by weight, e.g. about 10:1.

The present liposomes may contain various optional components in addition to the above-mentioned two essential components. For example, vitamin E α-tocopherol) and/or vitamin E acetate ester as an antioxidant may be added in an amount of 0.01 to 2 molar %, preferably 0.1 to 1 molar % relative to total amount of lipids.

For diagnostic compositions comprising liposomes containing the above-mentioned phospholipids, the concentration of total lipid is generally 20 mg/ml to 100 mg/ml, preferably 40 mg/ml to 90 mg/ml, and more preferably 50 mg/ml to 80 mg/ml, in order to enhance encapsulation of contrast agent in the liposomes.

Such contrast agents are preferably encapsulated in the liposomes in the form of an isotonic solution or suspension (relative to physiological osmotic pressure in the body) in an appropriate medium so that the liposomes are stably maintained in the body after administration. As a medium, water, buffer solution such as Tris-HCl buffer, phosphate buffer, citrate buffer or the like may be used.

A preferred pH range at room temperature is 6.5–8.5, more preferably 6.8–7.8. Where the contrast agent is a non-ionic X-ray contrast agent carrying multiple hydroxyl groups, e.g. iohexol, iodixanol or iopamidol, the buffer is preferably one having a negative temperature coefficient, as described in U.S. Pat. No. 4,278,654. Amine buffers have the required properties, particularly TRIS. This type of buffer has a lower pH at autoclaving temperatures, which increases the stability of the X-ray contrast agent during autoclaving, while returning to a physiologically more acceptable pH at room temperature. TRIS surprisingly also provides improved shelf life.

To obtain an isotonic solution or suspension, the contrast agent is dissolved or suspended in a medium at a concentration which provides an isotonic solution. In the case where a contrast agent alone cannot provide an isotonic solution because, for example, solubility of the contrast agent is low, other non-toxic water soluble substances, for example salts such as sodium chloride or sugars such as mantirol, glucose, sucrose, sorbitol or the like may be added to the medium so that an isotonic solution is formed.

As indicated above, one advantage of the compositions of the invention is their ability to withstand autoclaving. They also have a high encapsulation capacity and encapsulation ratio by virtue of their lipid composition.

In addition, as described hereinafter, the diagnostic compositions of the invention have good imaging properties and low side-effects.

The present liposomes can be produced by conventional procedures used for formation of multilamellar liposomes. These procedures include the Bangham method (J. Mol. Dial. 13, 238–252, 1965), the polyvalent alcohol method (Japanese Examined Patent Publication (Kokoku) No. 4-36734), the lipid-solution method (Japanese Examined Patent Publication (Kokoku) No. 4-36735), and the mechanochemical method (Japanese Examined Patent Publication (Kokoku) No. 4-28412).

Generally, desired multilamellar vesicles can be prepared by dissolving the above-mentioned phospholipids in a volatile organic solvent such as chloroform, methanol, dichloromethane, ethanol or the like, or a mixed solvent of said organic solvent and water, removing said solvent, mixing the resulting residue with an aqueous phase containing a contrast agent, and shaking or stirring the mixture.

As the step for removing solvent in the above-mentioned process, Bangham's method uses evaporation, but spray-drying or lyophilization also can be used.

In the above-mentioned liposome-preparing processes, the amount of the solvent used relative to lipid is not critical, and any amount which allows dissolution of lipid is acceptable. Removing solvent from the resulting mixture of lipid and solvent by evaporation can be carried out according to conventional procedure, such as evaporation under reduced pressure or, if necessary in the presence of inert gas. In practice, the above-mentioned volatile organic solvents may be used, if desired in mixed solvents comprising 10 volumes of said organic solvent and up to 1 volume of water.

To effect solvent removal by lyophilization, a solvent is selected which can be removed at a reduced pressure of about 0.005 to 0.1 Torr at a temperature lower than the freezing point of the solvent, typically −30° C. to −50° C. Where solvent removal is effected by spray drying the air pressure is typically controlled to 1.0 kg/cm$^2$ and the air flow rate to 0.35 cm$^2$/minute, the inlet temperature being adjusted to a temperature higher than the boiling point of the solvent used. For example, the solvent may be chloroform, the temperature may be adjusted to 60° to 90° C., and the spray drying may be effected according to conventional procedures.

The lipid residue thus obtained is mixed with an aqueous solution containing a contrast agent at a temperature equal to or higher than the phase transition temperature (Tc) of the lipid used, and then the mixture is vigorously or more gently shaken or stirred at a temperature equal to or higher than said Tc to produce the desired liposomes suspended in the aqueous solution containing the contrast agent. The electrolyte ion concentration in the aqueous solution containing the contrast agent should desirably be as low as possible to avoid adversely affecting the encapsulation efficiency etc.; generally the total concentration of positive and negative ions apart from the contrast agent is desirably not more than about 40 mM, preferably being not more than about 20 mM.

Although the particle size of the liposomes may be expressed by the number average particle size, the weight average particle size is preferably used in defining encapsulation capacity.

The average particle size of the present liposomes is usually 50 nm to 3,000 nm, preferably 150 nm to 1000 nm, and more preferably 200 nm to 500 nm. To obtain the above-mentioned desired particle size, liposomes having larger particle size may be passed through one or more filters having a predetermined pore size (e.g. about 1 micron) by an extrusion method (Biochem. Biophys. Acta Vol. 557, p 9 (1979)).

The liposomes of the invention contain at least a proportion having a multilamellar membrane. In general, when initially formed by the techniques described herein, the liposomes are multilamellar but when, in accordance with the preferred technique described above, the liposome suspension is passed through one or more filters, for example membrane filters, e.g. having a pore size around 1 micron, the outer layers of lipid are stripped away to leave a mixture of multilamellar and unilamellar liposomes. In general, the proportion of multilamellar liposomes is not less than 30%, preferably not less than 40% by weight. The multilamellar liposomes have some advantages in terms of stability but a relatively large proportion of unilamellar liposomes is acceptable, particularly since they may provide higher encapsulation capacity than multilamellar liposomes.

The liposomes thus prepared are present as a suspension in an aqueous medium (outer liquid), and are generally used as such as a diagnostic composition. The solution of the contrast agent which has not been encapsulated in liposomes during the formation of the liposomes is present as the outer liquid. Alternatively, the outer liquid may be replaced with another liquid, although the concentration of imaging agent should be the same in the outer liquid as in any inner liquid. In any case, the outer liquid (dispersion medium) is preferably isotonic relative to the internal aqueous phase of the liposomes. The electrolyte ion concentration in the thus-prepared liposome suspension should desirably be as low as possible; generally the total concentration of positive and negative ions apart from the contrast agent is desirably not more than about 40 mM, preferably being not more than about 20 mM, in order to enhance the stability of the liposomes on heat sterilisation and long term storage.

As noted above, the encapsulation capacity of the present liposomes is generally at least 5 ml/g lipid, preferably at least 6 ml/g.

When encapsulating an iodinated X-ray contrast agent by the method of the invention, the concentration of the contrast agent in the initial aqueous solution should desirably be high in order to give a product with a relatively high iodine/lipid ratio, thereby reducing costs and potential toxicity problems. However, according to the present invention, one preferred range for the weight ratio of iodine to lipid is 1.3–1.45. This is lower than some prior art ratios: WO 88/09165 gives a lower limit of 1.5.

The most preferred X-ray contrast compositions of the invention comprise hydrogenated phosphatidyl choline as the neutral phospholipid and hydrogenated phoshatidylserine as the charged phospholipid, preferably in the ratio 10:1. Such a composition may have an encapsulation capacity over 7 ml/g. The most preferred X-ray contrast agent for use in such compositions is iodixanol. The aqueous medium inside and outside the liposomes preferably contains about 400 mg iodixanol/ml, as well as an isotonicity adjusting agent such as sorbitol, a stabilising agent such as EDTANa$_2$Ca and TRIS buffer (pH about 7.4).

Liposome compositions for MR imaging may be prepared by the method of the invention by, for example, encapsulating an aqueous solution of a paramagnetic MR contrast agent such as GdHPDO3A or an aqueous suspension of a superparamagnetic MR contrast agent such as Fe$_3$O$_4$, e.g. having a particle size of about 10 nm; such a suspension may, for example, be prepared by controlled precipitation of magnetite from a mixture of iron (2+) and iron (3+) salts.

Liposome compositions in which a contrast agent is covalently linked to the liposome membrane may, for example, be prepared using methods analogous to those described in U.S. Pat. No. 5,135,737.

Gas-containing compositions for ultrasound imaging may be prepared in a variety of ways, e.g. using techniques similar to those described in the art for the preparation of gas-containing unilamellar and multilamellar vesicles. Such techniques are described in, for example, U.S. Pat. No. 4,544,545, U.S. Pat. No. 4,900,540, WO-A-9109629 and WO-A-9115244. Thus, for example, a solution of a pH-sensitive gas precursor may be encapsulated and the pH of the system subsequently changed to promote gas production within the liposome.

In such cases it may be advantageous to incorporate one or more ionophores into the membranes of the liposomes to aid transport of hydrogen ions or hydroxide ions across the membrane and thus facilitate the pH change—see, for example, the above-mentioned WO-A-9109629.

Alternatively a carbonate ester solution may be encapsulated together with a non-specific human esterase and the resulting liposomes incubated, e.g. at 37° C. for 5 days. The floating, carbon dioxide-containing liposomes may thereafter be separated and formulated as appropriate.

A further method for the preparation of gas-containing liposomes involves the application of an external pressure of gas to a suspension of preformed liposomes encapsulating an aqueous medium. In general the gas should be applied at very high pressure, e.g. at least about 5 atmospheres.

A still further method for preparation involves dispersing the selected phospholipids in an aqueous medium or a mixture of water and water soluble bioacceptable organic solvents known to stabilize phospholipid solutions, such as glycerol and propylenglycol, and agitating this solution vigorously in the presence of a selected gas or gas mixture.

Alternatively, the liposomes may be formed by ultrasonication of said phospholipid solution in presence of the selected gas or gas mixture.

Any biocompatible gas, e.g. as hereinbefore described, may be employed in making the ultrasound contrast agents of the invention.

In general, compositions of the invention, for use in any type of imaging, may if desired be modified with materials such as polyethyleneglycol to increase the circulation half-life of the liposomes. This may be particularly advantageous in applications involving cardiovascular imaging.

The following non-limitative examples serve to illustrate the invention.

Measurement Techniques (1) Measurement of Particle Size

The weight average particle size of the liposomes obtained was determined by a quasi elastic light scattering method using a Dynamic light scattering meter DLS (Otsuka Electronics Co., Ltd.).

(2) Measurement of Encapsulation Capacity

The volume of the internal aqueous phase of the liposomes was calculated by the proportion of iodixanol held in the liposomes; i.e. an encapsulation ratio of iodixanol is 40%, when in a 1 ml liposome preparation, 0.4 ml is the volume of the internal aqueous phase.

Encapsulation capacity is defined as the volume of internal aqueous phase per gram unit lipid. For example, where the concentration of the lipid of a liposome preparation is 0.056 g/ml, and the percentage of iodixanol in the liposomes is 40%, since 0.056 g of lipid carry 0.4 ml of the internal aqueous phase in 1 ml of liposomes, then the encapsulation capacity is 7.1 ml/g lipid.

The encapsulation ratio of sucrose in a liposome preparation was measured by the gel filtration method. Thus, liposome preparations were passed through a gel-filtration column (carrier Sephadex G50, Pharmacia; column diameter 16 mm; column height 300 mm) using physiological saline as the mobile phase, and the eluate was fractionated (2.5 ml/fraction). An aliquot of 0.8 ml was taken from each fraction, 2 ml of methanol was added thereto, followed by 1 ml of chloroform. The mixture was stirred once to make the whole transparent.

1 ml of chloroform was added thereto, and, after stirring, 1.2 ml of distilled water was added to the mixture, which was then stirred and centrifuged (3500 rpm, 10 minutes, room temperature) in a cooled centrifuge (Kuboka Shoji K.K., Type KR-702), and the concentration of iodixanol recovered in the upper phase (water-methanol phase) of the separated two phases was measured by absorbance at 246 nm. In the case where the concentration of iodixanol in the extract was high, the eluate was appropriately diluted with distilled water, 0.8 ml of an aliquot was taken and extracted with methanol, chloroform and distilled water.

The amount of iodixanol in the liposome fraction eluted in the void volume was divided by the total amount of iodixanol recovered in the eluate (the amount of iodixanol recovered in 25 fractions) to obtain an encapsulation ratio. Note that the end point of liposome fractionation was the fraction whose iodixanol concentration was minimal.

EXAMPLE 1

Encapsulation of X-ay Imaging Agent, Iodixanol 0.640 g of hydrogenated phosphatidylcholine derived from egg yolk (HEPC), 0.064 g of hydrogenated phosphatidylserine (HEPS) synthesized from HEPC, and 60 ml of a mixture of chloroform, methanol and water (volume ratio 100:20:0.1) were mixed in a flask. The mixture was heated on a water bath (65° C.) to dissolve the phospholipids, and the resulting solution was heated in a rotary evaporator at 60° C. to evaporate the solvent.

The residue was further dried in vacuum for 2 hours to form a lipid film. An aqueous solution containing iodixanol (1,3-bis(acetylamino)-N,N'-bis[3,5-bis(2,3-dihydroxypropylaminocarbonyl)-2,4,6-triiodophenyl]-2-hydroxypropane) (0.4 g/ml) and sucrose (0.05 g/ml) was heated to 65° C., and 10 ml of the heated solution was combined with the lipid film, and the mixture was stirred with a mixer for 10 minutes while heating at 65° C. This mixture was filtered once under pressure through a polycarbonate membrane filter having a pore size of 1.0 μm to yield multilamellar vesicles of the required size (MLV).

The MLV thus prepared was put into glass vials and autoclaved at 121° C. for 20 minutes for sterilization, and the results are shown in Table 1.

The encapsulation capacity was measured according to the method of (2) above. Weight average particle size was determined according to the method described in (1) above.

TABLE 1

| | Before autoclaving | After autoclaving |
|---|---|---|
| Particle size (nm) (Mean ± S.D.) | 260 ± 116 | 251 ± 120 |
| Encapsulation capacity (ml/g lipid) | 6.4 | 6.5 |
| Iodine/lipid weight ratio | 1.3 | 1.3 |
| Encapsulation ratio (%) | 45.1 | 45.8 |

EXAMPLE 2

Encapsulation of Iodixanol

A liposome formulation containing iodixanol was prepared according to the method described in Example 1.

The results are shown in Table 2.

TABLE 2

| Concentration in formulation (mg/ml) | | | Particle size (nm) (Mean ± S.D.) | | Encapsulation capacity (mg/g lipid) | | Iodine/lipid weight ratio | |
|---|---|---|---|---|---|---|---|---|
| | | | Before AC | After AC | Before AC | After AC | Before AC | After AC |
| HEPC | HEPS | Iodixanol | | | | | | |
| 64.0 | 6.4 | 400 | 260 + 116 | 251 + 120 | 6.4 | 6.4 | 1.3 | 1.3 |
| 64.0 | 6.4 | 200 | 125 ± 125 | 275 ± 118 | 7.8 | 8.0 | 0.8 | 0.8 |

Note: AC=autoclaving

EXAMPLE 3

The liposome suspension obtained in Example 1 was diluted with isotonic glucose to a concentration of 50 mg encapsulated iodine/ml. Upon dilution, the suspension turned milky white. No liposome aggregates could be observed upon microscopic analysis of the emulsion. No effect on the amount of encapsulated iodixanol and size distribution were observed following storage of the emulsion for one year.

EXAMPLE 4

The composition from Example 3 was injected intravenously into rats. The majority of the encapsulated iodixanol was confirmed to be distributed in the liver after injection, but high iodixanol concentration was also found in spleen. With time after injection, the tissue-associated iodixanol continuously decreased until eventually no iodixanol could be found in these two organs. All other organs showed iodixanol levels that decreased in parallel with the iodixanol level in blood. The majority of the injected iodixanol could be recovered in the urine.

EXAMPLE 5

The composition from Example 3 was injected intravenously into rats carrying multiple hepatic cancer metastases. At doses of 50 and 100 mg encapsulated iodine/kg, X ray attenuations of 42 and 62 HU respectively were observed in the normal regions of the liver, while attentuation in tumor metastases were minimally affected. Macroscopic analysis showed that detected tumors were smaller than 5 mm in diameter.

EXAMPLE 6

The composition from Example 3 was injected intravenously into groups of mice at doses of 200–7500 mg encapsulated iodine/kg body weight. Weight gain and mortality were followed over a 14 day period.

The results of the analysis showed that all animals survived injections of up to 3 g of liposome encapsulated iodixanol/kg. These animals showed no reduced weight gain during the observation period compared to non-injected animals. At doses of 4 and 5 g of liposome encapsulated iodixanol/kg, there was a slight, dose-dependent reduction in body weight gain, and deaths were observed. The $LD_{50}$ was estimated to be 5 g liposome encapsulated iodixanol/kg.

EXAMPLE 7

Following single and repeated (3 injections/week, 3 weeks) intravenous injections of the composition from Example 1 at doses from 100–1000 mg encapsulated iodine/kg in rats, the blood level of a variety of tissue-bound enzymes was measured, and the histology of all major organs analyzed at various timepoints. With respect to serum enzymes, only small effects were observed compared with saline injected control animals. Apart from a dose dependent increase in vacuolization of phagocytic cells in liver and spleen, no liposome-induced histological alterations were detected. The degree of vacuolization of the phagocytic cells decreased with time in parallel with the decrease in tissue associated iodixanol liver and spleen.

EXAMPLE 8

Iodixanol-containing Liposomes

A diagnostic composition comprising:

| | |
|---|---|
| Iodixanol (Total amount) | 400 mg/ml |
| (Iodine encapsulated) | 80 mg/ml |
| Sorbitol | 20 mg/ml |
| Trometamol (TRIS) | 0.097 mg/ml |
| EDTANa$_2$Ca | 0.1 mg/ml |
| Hydrogenated phosphatidylcholine | 51.2 mg/ml |
| Hydrogenated phosphatidylserine | 5.1 mg/ml |
| Water for injection ad | 1 ml (approx 0.9 ml) | was prepared by dissolving the phospholipid in chloroform/methanol/water (4:1:0.025, volume) and evaporating the solvent (rotary evaporation). An isotonic solution of iodixanol and sorbitol was made and heated to 60°–70° C. and this temperature was maintained during the remainder of the process. The phospholipid mixture was added with stirring, and the liposomes were formed. To control the size of the liposomes the preparation was homogenized (Rotor/Stator homogenizer). The liposomes were then extruded through 7 polycarbonate filters placed in series (pore diameter 1 μm).

The product was diluted with the isotonic solution of iodixanol and sorbitol, and trometamol and EDTA were added. The product was filled into glass vials and autoclaved (121° C., 15 minutes).

EXAMPLE 9

Iotrolan-containing Liposomes

The liposomes were prepared as described in Example 8, but iotrolan was used instead of iodixanol.

EXAMPLE 10

Iodixanol-containing Liposomes with Hydrogenated Phosphatidylglycerol

The liposomes were prepared as described in Example 8, but hydrogenated phosphatidyglycerol was used instead of hydrogenated phosphatidylserine.

EXAMPLE 11

MR Contrast Agent (gadolinium)

A lipid film of hydrogenated phosphatidylcholine and hydrogenated phosphatidylserine is prepared as described in Example 1.

10 ml of 0.5M solution of GdHPDO3A is heated to 65° C. This mixture is stirred with a mixer for 15 minutes while heating at 65° C. This mixture is filtered once under pressure through a polycarbonate membrane filter having a pore size of 1.0 µm to prepare multilamellar vesicles (MLV).

The MLV are put into glass vials and autoclaved at 121° C. for 20 minutes for sterilization.

The MLV contain GdHPDO3A.

EXAMPLE 12

MR Contrast Agent (manganese)

The liposomes are prepared according to Example 11 using a solution of the manganese chelate of 3,6-bis(N-(2,3-dihydroxypropyl)-N-methylcarbamoylmethyl]-3,6-diazaoctanedioic acid (0.07M) (prepared according to WO 93/21960 (Nycomed Imaging AS) instead of GdHPDO3A.

The MLV contain the manganese chelate.

EXAMPLE 13

MR Contrast Agent (dysprosium)

The liposomes are prepared according to Example 11 using a solution of DyDTPA-BMA (0.5M) instead of GdHPDO3A.

The MSV contain DyDTPA-BMA.

EXAMPLE 14

MR Contrast Agent (iron oxide)

The liposomes are prepared according to Example 11 using a suspension of magnetic iron oxide (10 mM particle size 10–30 nm) instead of GdHPDO3A.

EXAMPLE 15

Liposomal GDHPDO3A (HEPC-HEPS)

A pregenerated mixture of 640 mg of hydrogenated phosphatidylcholine derived from egg yolk (HEPC) and 64 mg of hydrogenated phosphatidylserine (PEEPS) synthesized from HEPC prepared as described in Example 1 was added to a vial containing 10 ml of a 5% aqueous solution of glucose (isotonic solution) containing 250 mMGdHPDO3A (gadoteridol). The mixture was stirred for 30 minutes at 65° C. and further kept at this temperature for an additional hour. The liposomal solution was subject to five freeze-thaw cycles and extruded five times at 65° C. through two stacked 400 nm polycarbonate filters to give the title product.

EXAMPLE 16

Liposomal GdHPDO3A (DPPC/DPPG)

A lipid blend of 640 mg dipalmitoylphosphatidylcholine (DPPC) and 64 mg dipalmitoylphosphatidylglycerol (DPPG) prepared as described in Example 1 was added to a vial containing 10 ml of a 5% aqueous solution of glucose (isotonic solution) containing 250 mMGdHPDO3A. The mixture was stirred at 50° C. for 30 minutes and further kept at this temperature for one hour. The liposome solution was subject to five freeze-thaw cycles and extruded five times at 50° C. through two stacked 400 nm polycarbonate filters.

EXAMPLE 17

Liposomal GdDTPA-BMA

The same procedure as in Example 15 was used, except that the aqueous solution contained 250 mM GdDTPA-BMA (gadodiamide) instead of GdHPDO3A.

EXAMPLE 18

Liposomal DyTTHA

The same procedure as in Example 15 was used, except that the aqueous solution contained 250 mM DyTTHA (dysprosium complex of triethylene tetramine hexa-acetic acid) instead of GdHPDO3A.

EXAMPLE 19

Ustrasound Contrast Agent

The liposomes are prepared according to Example 11 using saline instead of GdHPDO3A. The mixture is pressurized with nitrogen (70 psi) for 1 hour. The excess nitrogen is removed and the resulting mixture filtered through a polycarbonate membrane filter having a pore size of 1.0 µm.

The resulting MLV contain nitrogen gas.

EXAMPLE 20

The composition from Example 8 was injected intravenously into rats. At doses of 75 and 100 mg encapsulated iodine/kg X-ray attenuations of 47 and 70 HU respectively were observed in the liver.

EXAMPLE 21

The composition from Example 8 was injected intravenously into rats. The approximate $LD_{50}$ was found to be 2000 mg encapsulated iodine/kg.

We claim:

1. An autoclaved diagnostic composition for administration to human or animal subjects, said composition containing multilamellar liposomes, optionally together with unilamellar liposomes, said liposomes containing an aqueous phase containing at least one X-ray or magnetic resonance imaging contrast agent, said liposomes being suspended in an aqueous medium containing said contrast agent, said liposomes comprising a neutral phospholipid and a charged phospholipid, the average particle diameter of said liposomes being 50–3000 nm, the concentration of said contrast agent in said aqueous phase being substantially the same as that in the aqueous medium in which said liposomes are suspended during the autoclaving process, and the concentration of total lipid in said composition being 50 mg/mL to 80 mg/mL.

2. A diagnostic composition according to claim 1 wherein the aqueous medium in which the liposomes are suspended is isotonic.

3. A diagnostic composition according to claim 1 or claim 2 wherein the neutral phospholipid and/or the charged phospholipid comprises at least one substantially saturated fatty acid residue containing at least 14 carbon atoms.

4. A diagnostic composition according to claim 1 wherein the neutral phospholipid and/or the charged phospholipid comprises at least one substantially saturated fatty acid residue containing up to 28 carbon atoms.

5. A diagnostic composition according to claim 1 wherein the neutral phospholipid is a phosphatidylcholine.

6. A diagnostic composition according to claim 1 wherein the charged phospholipid is a phosphatidylserine, phosphatidylglycerol, phosphatidylinositol, phosphatidic acid or an ester of phosphatidic acid and an aminoalcohol.

7. A diagnostic composition according to claim 6 wherein the phosphatidyl group is a synthetic dipalmitoylphosphatidyl or distearoylphosphatidyl group.

8. A diagnostic composition according to claim 1 wherein the average particle diameter of the liposomes is 150 nm to 1000 nm.

9. A diagnostic composition according to claim 1 wherein the encapsulation capacity of the liposome is at least 5 ml/g.

10. A diagnostic composition according to claim 9 wherein the encapsulation capacity of the liposomes is at least 6 ml/g.

11. A diagnostic composition according to claim 1 wherein the weight ratio of the neutral phospholipid to the charged phospholipid is 60:1 to 4:1.

12. A diagnostic composition according to claim 1 wherein the concentration of total lipid is 20 mg/ml to 100 mg/ml.

13. A diagnostic composition according to claim 1 in which the X-ray contrast agent contains one or more iodinated phenyl groups or heavy metal clusters or chelates.

14. A diagnostic composition according to claim 13 wherein the contrast agent is iodixanol.

15. A diagnostic composition according to claim 1 wherein said contrast agent is a magnetic resonance imaging contrast agent.

16. A diagnostic composition according to claim 15 wherein said magnetic resonance imaging contrast agent contains manganese.

17. A diagnostic composition according to claim 15 wherein said magnetic resonance imaging contrast agent is a gadolinium chelate.

18. In a process for the production of an autoclaved diagnostic imaging contrast agent composition according to claim 1, wherein the improvement comprises dissolving a neutral phospholipid and a charged phospholipid in a solvent, removing the solvent to obtain a residue, mixing the residue with an aqueous solution containing an X-ray or magnetic resonance imaging contrast agent whereby liposomes are formed encapsulating said contrast agent, and autoclaving the mixture produced.

19. A process as claimed in claim 18 in which the liposomes so formed are extruded through a membrane filter to reduce their size.

* * * * *